United States Patent [19]

Guglielmo et al.

[11] Patent Number: 5,367,103
[45] Date of Patent: Nov. 22, 1994

[54] PROCESS FOR PURIFYING FLUOROETHANES AND CHLOROFLUOROETHANES

[75] Inventors: Giorgio Guglielmo, Venice; Giampaolo Gambaretto, Padova, both of Italy

[73] Assignee: Ausimont S.p.A., Milan, Italy

[21] Appl. No.: 995,128

[22] Filed: Dec. 22, 1992

[30] Foreign Application Priority Data

Dec. 23, 1991 [IT]  Italy ................ MI91A 003466

[51] Int. Cl.$^5$ ................ C07C 17/38; C07C 17/08
[52] U.S. Cl. .................... 570/177; 570/166; 570/167; 570/168; 570/169; 570/175
[58] Field of Search ............... 570/177, 175, 166, 167, 570/168, 169

[56] References Cited

U.S. PATENT DOCUMENTS 5,001,287  3/1991  Fernandez et al. ............ 570/178

FOREIGN PATENT DOCUMENTS 0219823  4/1987  European Pat. Off. .......... 570/175

*Primary Examiner*—Alan Siegel
*Attorney, Agent, or Firm*—Bryan Cave

[57] ABSTRACT

1,1,1.Trifluoro-2-fluoroethane (HFC 134A), respectively 1,1,1-trifluoro-2, 2-dichloroethane (HCFC 123) 1,1,1-trifluoro-2-chloro, 2-fluoroethane (HCFC 124) and pentafluoroethane (HFC 125), are purified from impurities respectively consisting of 1,1-difluoro-2-chloroethylene (HCFC 1122) and of difluorodichloroethylene (CFC 1112A and CFC 1112), by reacting in the liquid state respectively HFC 134A or HCFC 123, HCFC 124 and HFC 125 containing the relative impurities, with elemental fluorine, at temperatures ranging from −80° to −40° C.

9 Claims, No Drawings

PROCESS FOR PURIFYING FLUOROETHANES AND CHLOROFLUOROETHANES

The present invention relates to a process for obtaining the purification of fluorocarbons and chlorofluorocarbons containing hydrogen (HFC and HCFC) from impurities consisting of olefinic compounds, and in particular chloroolefinic compounds, which, as is known, give rise to toxicity and chemical stability problems.

In particular such process relates to the purification of 1,1,1-trifluoro-2-fluoroethane and the isomers thereof (hereinafter referred to as 134a) from impurities consisting of 1,1-difluoro-2-chloroethylene (hereinafter referred to as 1122), as well as the purification of 1,1,1-trifluoro-2,2-dichloroethane referred to as 123), of 1,1,1-trifluoro, 2-chloro, 2-fluoroethane (referred to as 124) and their isomers, and of pentafluoroethane (referred to as 125) from impurities consisting of $CF_2=CCl_2$ (referred to as 1112a) and, in case, also of its isomers $CFCl=CFCl$ (referred to as 1112).

It is known how to prepare 134a by fluorination of $CF_3CH_2Cl$ (hereinafter referred to as 133a). Such a preparation method always leads also to the obtainment of 1122, the toxicity of which is known.

Therefore the need is felt to have available 134a as free as possible from 1122.

The separation of 1122 from 134a by means of physical methods, for example fractional distillation, is extremely difficult.

It has been suggested to convert the 1122 contained in the 134a into more easily separable compounds by means of oxidation with hydrogen peroxide, or with permanganates (U.S. Pat. No. 4,129,603). Such a solution, however, is not very practical as it involves several onerous treatments in moist conditions, with production of great volumes of effluents difficult to be disposed off, particularly when great volumes of 134a to be purified must be treated.

Other suggested methods, such as chlorination with elemental chlorine in the presence of U.V. radiations (U.S. Pat. No. 4,948,479) and catalytic hydrogenation (U.S. Pat. No. 5,001,287) are not applicable on an industrial scale.

According to U.S. Pat. No. 4,158,675 it is possible to separate 1122 from 134a, up to residual concentrations of 1122 lower than 10 p.p.m., by reacting 1122 with HF in the presence of a catalyst consisting of amorphous $Cr_2O_3$, so as to convert it to $CF_3CH_2Cl$, which, having a boiling temperature higher by 30°°C. than the one of 134a, can be subsequently distilled-off from the latter.

In this case, however, the Applicant has observed that during the reactivation of the catalyst with air, considerable amounts of volatile and very toxic hexavalent chrome oxyfluoride ($CrO_2F_2$) from and are then dispersed in the environment. Furthermore, another drawback of such process resides in the necessity that the reagent mixture should be prevailingly composed of HF; such a fact—considering that the mixture coming from the 134a production reaction and containing little more than 3% of 134a must be fed to the purification reactor—strongly limits the capability of the process of meeting great production requirements.

A patent application filed concurrently herewith (U.S. application Ser. No. 07/995,127) describes a process for separating the 1122 impurities from 134a, which process consists in reacting the 1122 contained in the mixture with 134a, with HF in hot conditions, in the presence of a catalyst consisting of $Cr_2O_3$ substantially in the crystalline form.

This method permits reducing the 1122 content in the 134a to values below 100 p.p.m., however it is subject to the disadvantage of requiring frequent reactivation of the catalyst in order to maintain such purification values.

As regards the separation of 1112a and of 1112 from 123, 124 and 125 specific methods of some importance are not known.

Also in this case the separation via distillation is very difficult.

It has not surprisingly been found by the Applicant that by treating 134a polluted by 1122, or 123, 124 and 125 polluted by 1112a and/or 1112, with elemental fluorine, in the liquid phase at temperatures lower than $-40°$ C., and generally ranging from $-80°$ C. to $-40°$ C., it is possible to selectively and quantitatively obtain the addition of fluorine to the double bond of the aforesaid olefinic compounds, with formation of saturated products, which are easily separable from 134a and from 123, 124 and 125 respectively, by means of distillation.

In particular, 1112 is converted into $CF_3CHClF$ (hereinafter referred to as 124), while 1112a and 1112 are respectively converted into $CF_3CFCl_2$ (designated as 114a) and $CF_2Cl\ CF_2Cl$ (designated as 114).

Thus, an object of the present invention is a process for purifying 134a from impurities consisting of 1122, and 123, 124 and 125 from impurities consisting of 1112a and, in case, also of 1112, which process consists in reacting, in the liquid state, respectively 134a or 123, 124 and 125, singly or in admixture with each other, containing the relative impurities, with elemental fluorine at temperatures ranging from $-80°$ C. to $-40°$ C.

It was not obvious that fluorine, under such conditions, would add to the olefin without reacting with the hydrogenated compounds present therein, such as 134a, 123, 124 and 125.

The reaction can be conducted at atmospheric pressure or at a higher pressure, generally not exceeding 10 abs. atm., and preferably not exceeding 2 abs. atm.

Preferred reaction temperatures are those ranging from $-70°$ C. to $-50°$ C.

Generally, the reaction is carried out by bubbling the gaseous fluorine, preferably diluted with nitrogen in $F_2/N_2$ volume ratios ranging from 1/99 to 20/80 and preferably from 1/99 to 5/95, into the organic mixture in the liquid state.

134a, 123, 124 and 125 to be purified according to the process of the invention can comprise, besides the respective impurities mentioned above, also, other products which had been utilized or had been formed during the reaction for preparing such compounds.

For example, 134a, formed by hydrofluorination of trichloroethylene and/or of 133a(1,1,1-trifluoro-2-chloroethane), can contain, besides 1122, compounds such as trichloroethylene, $CFCl=CHCl$ (1121), $CF_3ClCH_2Cl$ (132), $CF_3CH_3$ (143) and so on.

123 and 124, prepared by hydrofluorination of tetrachloroethylene, can therefore contain, besides 1112a and 1112, compounds such as tetrachloroethylene, $CFCl=CCl_2$ (1111), $CF_2Cl—CHCl_2$ (122) and so on.

The same applies to 125, obtained by hydrofluorination of tetrachloroethylene or by dismutation of 124.

The process according to the present invention can be conducted continuously, semicontinuously or discontinuously.

After the reaction, the impurities can be separated from 134a, 123, 124 and 125 and distillation.

The following examples are given to illustrate the present invention, but not to limit the scope thereof.

EXAMPLE 1

Into a glass reactor having a 500 ml volume, equipped with a stirrer and an outer cooling jacket, there were introduced 500 g of 134a containing 80 p.p.m. by weight of $CF_2=CHCl$. Maintaining the reactor at $-60°$ C., at atmospheric pressure and under stirring, a gaseous mixture of $F_2/N_2$ (at 1% by volume of $F_2$) was fed (through a plunging pipe) at a flowrate of 1 normal liters per hours (hereinafter, N l/hour).

After 60 minutes, during which a fluorine amount higher by 10% than the stoichiometric amount was fed, the concentration of 124 (which was absent in the starting sample) was equal to 90 p.p.m. by weight.

EXAMPLE 2

The reaction was carried out as in Example 1, but with $F_2N_2$ flowrates of 6N l/h, and the reaction was terminated after 10 minutes. The same results were obtained.

EXAMPLE 3

The reaction was carried out as in Example 1, but with 134a containing 100 p.p.m. by weight of $CF_2=CHCl$, and with a $F_2/N_2$ flowrate (at 5% by volume of $F_2$) of 5N l/h. After 30 minutes (with an amount of $F_2$ feed higher by 10% than the stoichiometric amount), an amount of $CF_2=CHCl \leq 10$ p.p.m. by weight and an amount of 124 equal to 120 p.p.m. by weight were found in 134a.

EXAMPLE 4

The reaction was carried out as in Example 3, but at a pressure of 1.5 abs. atm., obtaining the same results as in such example.

EXAMPLE 5

Into the reactor of Example 1 there were introduced 370 g of trifluorodichloroethane (CFC 123), in the form of a mixture of the isomers, containing 0.22% by weight of dichlorodifluoroethylene (CFC-1112).

At $-60°$ C. and at atmospheric pressure there were fed, through a plunging pipe, 83 l/h of a fluorine/nitrogen mixture containing 1.3% by volume of $F_2$.

After 90 minutes, during which a fluorine amount higher by 8% than the stoichiometric mixture was fed, GLC analysis revealed the complete disappearance of CFC-1112 and its integral conversion to dichlorotetrafluoroethane (CFC-114).

We claim:

1. A process for purifying a mixture selected from the group consisting of:
   (a) a mixture comprising 1,1,1-trifluoro-2-fluoroethane or the isomers thereof with a 1,1-difluoro-2-chloroethylene impurity; and
   (b) a mixture comprising 1,1,1-trifluoro-2,2-dichloroethane or the isomers thereof, 1,1,1-trifluoro-2-chloro, 2-fluoroethane or the isomers thereof or pentafluoroethane, with impurities selected from the group consisting of 1,1-difluoro-2,2-dichlorethylene, 1,2-difluoro-1,2-dichlorethylene and mixtures thereof;
   which consisting essentially of reacting the mixture with elemental fluorine in the liquid phase and at temperature ranging from $-80°$ C. to $-40°$ C. to selectively and quantitatively add the fluorine to the double bond of the olefinic impurity or impurities.

2. The process of claim 1, wherein the reaction is carried out under atmospheric pressure or at higher pressures not exceeding 10 atmospheres absolute and at temperatures of from $-70°$ to $-50°$ Celsius.

3. The process of claim 1, wherein the reaction is carried out by bubbling the gaseous fluorine diluted with nitrogen in $F_2/N_2$ volume ratios ranging from 1/99 to 20/80 into the mixture in the liquid phase.

4. The process of claim 1, wherein mixture (a) is purified.

5. The process of claim 4, wherein the reaction is carried out under atmospheric pressure or at higher pressures not exceeding 10 atmospheres absolute and at temperatures of from $-70°$ to $-50°$ Celsius.

6. The process of claim 4, wherein the reaction is carried out by bubbling the gaseous fluorine diluted with nitrogen in $F_2/N_2$ volume ratios ranging from 1/99 to 20/80 into the mixture in the liquid phase.

7. The process of claim 1, wherein mixture (b) is purified.

8. The process of claim 7, wherein the reaction is carried out under atmospheric pressure or at higher pressures not exceeding 10 atmospheres absolute and at temperatures of from $-70°$ to $-50°$ Celsius.

9. The process of claim 7, wherein the reaction is carried out by bubbling the gaseous fluorine diluted with nitrogen in $F_2/N_2$ volume ratios ranging from 1/99 to 20/80 into the mixture in the liquid phase.

* * * * *